US005376659A

United States Patent [19]

Liebeschuetz et al.

[11] Patent Number: 5,376,659

[45] Date of Patent: Dec. 27, 1994

[54] SUBSTITUTED GUANIDINE AND AMIDINE COMPOUNDS, AND FUNGICIDAL USE

[75] Inventors: John W. Liebeschuetz, Wantage, Great Britain; Michel J. Jung, Tradate, Italy

[73] Assignee: DowElanco, Indianapolis, Ind.

[21] Appl. No.: 821,521

[22] Filed: Jan. 14, 1992

Related U.S. Application Data

[63] Continuation-in-part of Ser. No. 453,632, Dec. 20, 1989, abandoned.

[51] Int. Cl.$^5$ .................. C07D 401/04; C07D 403/04; A01N 43/54; A01N 43/56

[52] U.S. Cl. .................................... 514/275; 514/402; 514/422; 514/343; 514/218; 514/212; 548/314.7; 548/518; 548/524; 546/281; 544/330; 544/332; 540/553; 540/602

[58] Field of Search ............... 514/275, 402, 422, 343, 514/275, 218, 212; 544/330, 332, 335; 548/314.7; 546/281; 540/553

[56] References Cited

U.S. PATENT DOCUMENTS 2,988,478 12/1958 Gordon ................................ 167/33

FOREIGN PATENT DOCUMENTS 197976 8/1979 Czechoslovakia .

OTHER PUBLICATIONS

Intl. Pest Control, Hudson, Ojo, & Pianka, pp. 148–155 (1986) Nov./Dec.

*Primary Examiner*—John M. Ford
*Attorney, Agent, or Firm*—S. Preston Jones; Kenneth L. Loertscher

[57] ABSTRACT

The present invention relates to novel substituted guanidine and amidine compounds, their preparation and their use in the kill and control of fungal organisms which infest plants.

22 Claims, No Drawings

SUBSTITUTED GUANIDINE AND AMIDINE COMPOUNDS, AND FUNGICIDAL USE

CROSS-REFERENCE TO RELATED APPLICATIONS

This application is a continuation-in-part of application Ser. No. 07/453,632, filed Dec. 20, 1989, now abandoned.

FIELD OF THE INVENTION

This invention relates to novel chemical compounds containing a guanidine or an amidine grouping and the fungicidal activity thereof.

PRIOR ART

Many substituted guanidines are known to have antifungal and antibacterial activity. A detailed review of the antifungal activity of such compounds is found in International Pest Control, November/December 1986, pp 148-155 (H. R. Hudson, I. A. O. Ojo and M. Pianka).

Fungicidally effective amidine-type compounds are also disclosed in Czechoslovakian Patent No. 197976. Fungicidally active guanidine-containing compounds are also disclosed in U.S. Pat. No. 2,988,478.

SUMMARY OF THE INVENTION

In accordance with the present invention, there are provided novel chemical compounds containing a guanidine or an amidine grouping which compounds are active material in fungicidal compositions useful in killing and controlling various fungal organisms which infest plants. Many of these compounds not only kill and control fungal organisms, but also provide systemic protection; certain forms of the compounds which are very water soluble allow for easier formulating responses.

The compounds of the present invention correspond either to the general formula

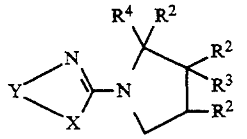
I or an agriculturally acceptable salt of the compounds of Formula I corresponding to the general formula,

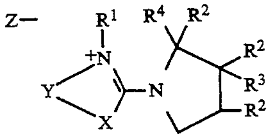
II wherein

- $R^1$ is hydrogen or $C_1$–$C_3$ alkyl; $R^2$, each independently, is hydrogen or $C_1$–$C_4$ alkyl;
- $R^3$ is a $C_4$–$C_{20}$ alkyl group, a $C_4$–$C_{20}$ alkenyl group, a phenyl group, a phenyl-$C_1$–$C_3$ alkylene group or a phenyl-$C_2$–$C_3$ alkenylene group wherein the phenyl ring can be substituted with from 1 to 5 halogen atoms, $C_1$–$C_6$ alkyl, $C_1$–$C_6$ alkoxy groups, trihalomethyl groups, phenyl groups or phenoxy groups;
- $R_4$ is hydrogen or $C_1$–$C_4$ alkyl;
- X is a group of the formula —$C(R^7R^7)$—, wherein each $R^7$ independently is hydrogen, $C_1$–$C_4$ alkyl, $C_1$–$C_4$ hydroxyalkyl, $C_2$–$C_4$ alkoxyalkyl or a group of the formula $$-(CH_2)_q-O-C(O)-R^8,$$

wherein q is the integer 1, 2 or 3, and $R^8$ is methyl or ethyl or X is a group of the formula —$N(R^9)$—, wherein $R^9$ is H, or $C_1$–$C_3$ alkyl;
- Y is a group of the formula —$(C(R^7R^7))_n$—, wherein each $R^7$ independently is as defined above, n is the integer 2, 3, or 4; and
- Z is an anion from the group consisting of the bromide, chloride, iodide, acetate, stearate, benzoate, and dodecylbenzenesulphonate.

It will of course be appreciated that although the compounds of the Formulae I and II are illustrated as containing a simple double bond, in practice considerable delocalization of the double bond structure will take place over the two or three nitrogen atoms of the compounds.

Since the compounds of the invention can contain two or three basic nitrogen atoms, they can exist either in the form of the free base or an agriculturally acceptable salt, such as, for example, a quaternary salt or an acid addition-salt. The compound can thus exist in tautomeric forms, all of which are within the scope of the present invention.

In the compounds of Formulae I and II,

- $R^1$ is preferably hydrogen, methyl or ethyl, and more preferably hydrogen;
- $R^2$ is preferably hydrogen or methyl, and more preferably hydrogen;
- $R^3$ group is preferably a phenyl group optionally substituted with from 1 to 5 halogen atoms, $C_1$–$C_6$ alkyl or $C_1$–$C_6$ alkoxy groups, trihalomethyl, phenyl or phenoxy groups, and more preferably a phenyl group substituted in the No. 4 ring position with a $C_3$–$C_6$ alkyl group;
- $R^4$ is preferably methyl;
- X in both Formula I and II can be an optionally substituted carbon atom, in which case the compound is of the amidine type, or an optionally substituted nitrogen atom, in which case the compound is of the guanidine type;
- Y is preferably a group of the formula —$(C(R^7R^7))_3$—, wherein $R^7$ is as defined above, preferably hydrogen or methyl, and more preferably a group of the formula —$(CH_2)_3$—, or —$CHMeCH_2CHMe$—, wherein Me is methyl;
- $R^7$, independently in each occurrence, is preferably hydrogen or methyl, and more preferably hydrogen;
- $R^9$ is preferably hydrogen or methyl, more preferably hydrogen; and
- Z—is an anion such as the bromide, chloride. iodide, acetate, stearate, benzoate or dodecylbenzenesulfonate, with chloride being preferred.

The ring containing the guanidine/amidine group is preferably six membered, i.e., n in the definition of Y is preferably 3.

The terms alkyl, alkoxy, alkenyl, alkylene, alkenylene and the like, as used herein are employed in their common chemical meaning and are intended to include within their scope both straight and branched chained forms of said groups, and the terms alkenyl, alkylene, alkenylene and the like are intended to cover groups containing one or more than one double bond. The terms halogen and halo are used herein to designate bromine, chlorine, fluorine and iodine atoms.

It will be appreciated that certain combinations of substituent groups for compounds which fall within the generic definition of the substituents set forth for Formulae I and II may be impracticable to prepare due to known steric considerations and such compounds are not included within the scope of the invention.

The compounds of Formula I may be prepared by reacting a compound of the formula

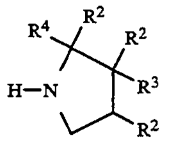

III with a compound of the formula

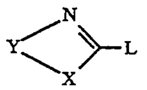

IV wherein $R^1$, each $R^2$ independently, $R^3$ and $R^4$ are as defined hereinabove, and L is a suitable leaving group, such as, for example, an alkoxy, an alkylthio (preferably methylthio or ethylthio), phenylthio or sulfonic acid ($SO_3H$) group. The reaction may be carried out at a temperature of from 50° to 200° C., in the presence of a suitable organic solvent, such as, for example, an alkanol such as ethanol, n-propanol, isopropanol, n-butanol, isobutanol, n-pentanol or n-hexanol or the reaction may be carried out in the absence of solvent.

This method is especially useful for the preparation of the amidine-type compounds in accordance with the invention (i.e. those in which X is a group of the formula —$C(R^7R^7)$—), in which case L is preferably an alkoxy group.

The salts of the amidine-type compounds in accordance with the invention (i.e. those in which X is a group of the formula —$C(R^7R^7)$— and wherein $R^1$ is hydrogen and $R^2$, $R^3$, $R^4$, $R^7$, Z—and Y, are as defined hereinabove), and which correspond to the formula

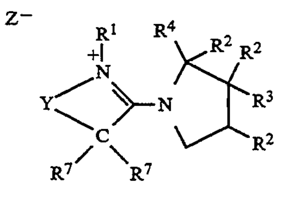

V may be prepared from an amidine of Formula I (i.e. where X is a group of the formula —$C(R^7R^7)$— by treatment, at room temperature, with an equivalent of an appropriate acid of the formula HZ wherein Z is as defined hereinabove) in an appropriate polar solvent such as ethanol, tetrahydrofuran or water.

The salts of the amidine-type compounds in accordance with the invention (i.e. those wherein $R^1$ is $C_1$–$C_3$ alkyl and $R^2$, $R^3$, $R^4$, $R^7$, Z— and Y, are as defined hereinabove may be prepared from an amidine of Formula I, where $R^1$ is hydrogen, by treatment at about room temperature including a slightly elevated temperature, with about an equivalent including a slight excess of an appropriate quaternizing agent $R^1Z$ wherein $R^1$ is $C_1$–$C_3$ alkyl and Z is as defined hereinabove in an appropriate polar solvent such as methanol or the reaction may be conducted neat.

The halide salts of the guanidine-type compounds in accordance with the invention (i.e. those in which X is a group of the formula —$N(R^9)$—; and Y, $R^2$, $R^3$, $R^4$, $R^7$ and $R^9$ are as defined hereinabove, and where Za— is bromo, chloro or iodo) and which correspond to the formula

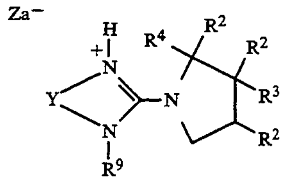

VI may be prepared using the above method set forth for preparing the compounds of Formula I, in which case, L is preferably an alkylthio group, and the compound of the Formula IV is used in the form of a halide salt, wherein the term "halide" represents bromo, chloro or iodo.

The non halide salts of the compounds of Formula II may be prepared from the above prepared halide salts employing conventional room temperature exchange techniques whereby a halide salt is dissolved in a solvent such as, for example, chloroform, washing the thus formed mixture with a strong (2 molar) sodium hydroxide solution and treating the organic solution with the appropriate organic acid to give the desired salt.

The salts of certain of the guanidine-type compounds (i.e. those in which X is a group of the formula —$N(R^9)$— and $R^9$ is hydrogen; Y is —$(CR^7)_3$—; and $R^2$, $R^3$, $R^4$, $R^7$ and Z are as defined hereinabove ), and which correspond to the formula

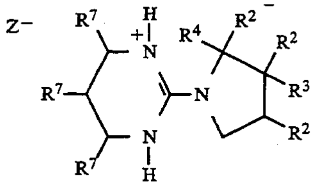

VII may be prepared by reducing a compound of formula

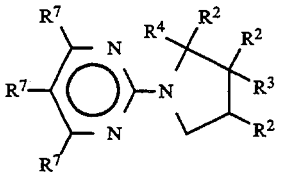

VIII preferably utilizing hydrogen and a conventional metallic hydrogenation catalyst such as palladium, platinum, rhodium or ruthenium in the presence of an acid HZ wherein Z is as defined hereinabove. Representative acids include hydrobromic, hydrochloric, hydroiodide, dodecylbenzenesulfonic, benzoic and acetic acid. The reaction may be carried out at any suitable temperature and pressure, preferably room temperature and atmospheric pressure, in a polar solvent, such as, for example, water, methanol, ethanol or mixtures thereof.

The compound of Formula VIII may be prepared by reacting a compound of the formula

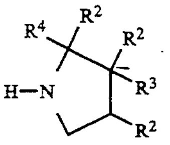

III with a compound of the formula

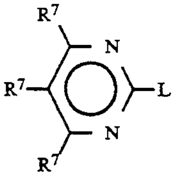

IX wherein each $R^2$ independently, $R^3$, $R^4$ and $R^7$ each independently is as defined hereinabove and L is a suitable leaving group as defined hereinabove. The reaction of the compound of Formula III with the compound of Formula IX may be carried out in a polar solvent, for example, an alkanol such as ethanol, n-propanol, n-butanol, n-pentanol or n-hexanol or a material such as dimethylformamide or dimethylsulfoxide in the presence of a base conventionally used as an acid acceptor. Such bases include pyridine and trialkylamines such as triethylamine and ethyldiisopropylamine, at a temperature of from 50° to 200° C.

Compounds of Formula III may in turn be prepared by the internal condensation of a compound of the formula

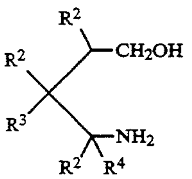

X preferably in the presence of triphenylphosphine and diethyl azadicarboxylate. The internal condensation may be carried out in an organic solvent, for example, an ether such as tetrahydrofuran (THF), at a temperature of from 0° to 150° C.

Compounds of the Formula X may be prepared by the reaction of a compound of the formula $R^4R^2CH.NO_2$ with a compound of the formula $R^2R^3C{=}CR^2CO_2Et$ preferably in the presence of a mild base such as tetrabutyl ammonium hydroxide or tetrabutyl ammonium fluoride at a temperature of from 25° to 150° C., followed by reduction of the nitro and ester groups, for example, using a metal hydride such as $LiAlH_4$. The reduction may be carried out at a temperature of from minus 80° to 100° C. in an inert solvent, for example, an ether.

The compound of formula $R^2R^3C{=}CR^2CO_2Et$ may in turn be prepared by reaction of an ether compound of the formula $C(O)R^2R^3$ with a compound of the formula $(EtO)_2PCHR^2CO_2Et$ in presence of a base such as sodium hydride. The reaction may be carried out in a solvent such as diethyl ether or THF at temperatures of from 0°-50° C.

A number of preferred embodiments of the invention are illustrated in the following Examples.

Example 1

Cis N-(tetrahydropyrimidin-2-yl)-2-methyl-3-(4-t-butylphenyl)pyrrolidine: Acetic Acid Salt

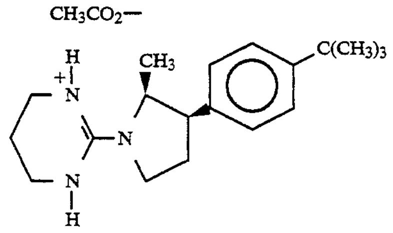

(a) Preparation of ethyl 3-(4-t-butylphenyl)propenoate

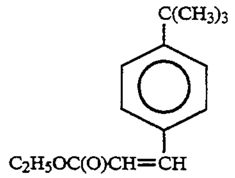

2.42 g (0.06 mol) of sodium hydride (60 percent in mineral oil) was washed with hexane under nitrogen. 30 mL of tetrahydrofuran was added thereto and the mixture cooled to 0° C. 13.8 g (0.06 mol) of triethylphosphonoacetate in 50 mL of THF was then added dropwise, with stirring. Half an hour after completion of the addition, 10 g (0.06 mol) of 4-t-butylbenzaldehyde in 40 mL THF was added dropwise. The mixture was allowed to warm to room temperature, the solvent was evaporated off and the residue was taken up in ethylacetate. The resulting solution was washed four times with water, dried, filtered and the solvent removed under reduced pressure to afford 12 g (81 percent of theoretical) of the crude product in the form of an oil. The NMR and IR spectra of the product were consistent with the expected structure.

(b) Preparation of Ethyl 4-nitro-3-(4-t-butylphenyl)pentanoate

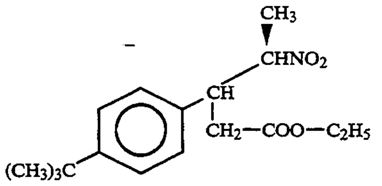

6 g (0.026 mol) of the compound prepared in (a) above, 35 mL (0.49 mol) of nitroethane and 6 mL of a 40 percent solution of tetrabutylammonium hydroxide in methanol were mixed and refluxed together under nitrogen for three hours. The resulting mixture was poured into 85 mL of a 10 percent aqueous ammonium chloride solution and the resulting solution was thoroughly extracted with ethylacetate. The organic solution was washed three times with 10 percent $NHCl_4$, dried, filtered and the solvent evaporated off to afford 4.2 g (53 percent of theoretical) of the crude product in the form of an oil. Elemental analysis indicated the following:

| | percent | | |
|---|---|---|---|
| | C | H | N |
| calculated | 66.4 | 8.20 | 4.6 |
| found | 66.4 | 8.30 | 4.6. |

The NMR and IR spectra of the product were consistent with the expected structure.

(c) Preparation of 3-(4-t-butylphenyl)-4-aminopentan-1-ol

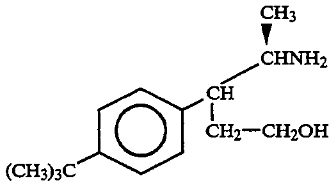

6.5 g (0.021 mol) of the nitro ester prepared as in (b) above was added dropwise to 5 g (0.18 mol) of lithium aluminum hydride suspended in 200 mL of anhydrous diethyl ether, under nitrogen with stirring. The mixture was then refluxed for ten hours. A 50 percent $H_2O$/THF solution was added dropwise and slowly with vigorous stirring until effervescence ceased. 1N sodium hydroxide solution was then added dropwise until the slurry coagulated to a coarse sandy consistency. The mixture was filtered and the solid washed with diethyl ether. The organic fractions were combined, washed with water, dried, filtered and the solvent evaporated off at reduced pressure to afford 4 g (80 percent of theoretical) of the crude product in the form of a gum. The NMR and IR spectra of the product were consistent with the expected structure, and indicated a mixture of the two possible diastereoisomers in a ratio of 2:1.

(d) Preparation of 3-(4-t-butylphenyl)-2-methylpyrrolidine

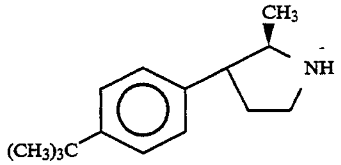

4.2 g (0.018 mol) of the aminoalcohol prepared in (c), 4.69 g (0.018 mol) of triphenylphosphine and 3.1 g (0.018 mol) of diethyl azodicarboxylate were dissolved in 100 mL THF. 2 drops of glacial acetic acid were added and the solution refluxed for two hours. During this time the initially red solution became yellow. On cooling, hexane was added dropwise until precipitation started. The mixture was then cooled in the freezer and the crystalline precipitate filtered off. The solvent was removed under reduced pressure and the residue taken up in chloroform and washed with water. The organic layer was dried with $MgSO_4$, filtered, the solvent evaporated off under reduced pressure and the residue vacuum distilled (130° C. at 2 mm Hg) to afford 3.0 g (77 percent of theoretical) of the crude product in the form of a mobile oil. The NMR and IR spectra of the product were consistent with the expected structure and indicated a mixture of the two possible diastereoisomers were present in a ratio of 3:1.

(e) Preparation of cis and trans 1-(pyrimidin-2-yl)-2-methyl-3-(4-t-butylphenyl)-pyrrolidine

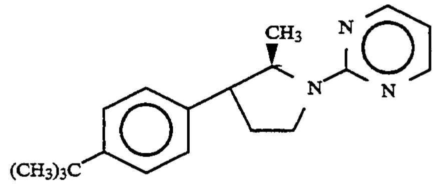

1.4 g (0.0065 mol) of the substituted pyrrolidine prepared in (d), 0.74 (0.0065 mol) g of chloropyrimidine and 0.83 g (0.0065 mol) of diisopropylethylamine were mixed together in 40 mL pentanol and refluxed under nitrogen for six hours. The pentanol was distilled off under reduced pressure. The residue was taken up in dichloromethane and washed three times with water. The solution was dried over $MgSO_4$ and filtered. The solvent was evaporated off under reduced pressure. Column chromatography using a toluene/ethylacetate mixture as the eluent afforded both the cis and trans isomers stereochemically pure in a 2:1 ratio in a yield of 1.36 g (70 percent of theoretical). Elemental analysis indicated the following:

| | percent | | |
|---|---|---|---|
| | C | H | N |
| calculated | 77.2 | 8.55 | 14.2 |
| found | 76.7 | 8.65 | 13.4. |

(f)Preparation of Final Product (cis N-(tetrahydropyrimidin-2-yl))-2-methyl-3-(4-t-butylphenyl)pyrrolidine Acetic Acid Salt)

540 mg (0.0018 mol) of the cis pyrimidinylamine prepared above in (e) was dissolved in 20 mL of ethanol with 100 mg of 10 percent Pd/C and 0.5 mL (0.09 mol) of acetic acid added thereto. The mixture was hydrogenated at room temperature and pressure with shaking for eight hours until the theoretical quantity of hydrogen had been absorbed. The mixture was passed through celite and the solvent removed by evaporation under reduced pressure. After vacuum drying the residue, 0.5 g (75 percent of theoretical) of a gum was collected. The NMR and IR spectra of the product were consistent with the expected structure.

Example 2

Preparation of trans N-(tetrahydropyrimidin-2-yl)-2-methyl-3-(4-t-butylphenyl)-pyrrolidine: Acetic Acid Salt

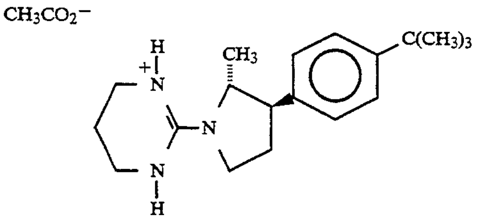

The trans product from step (e) in Example 1 was subjected to the same procedure as in step (f) to yield 0.25 g (76 percent of theoretical) of the trans isomer as the product. The NMR and IR spectra of the product were consistent with the expected structure.

By an analogous method, using one or more of hydrochloric acid in place of acetic acid in step (f), 4,6-dimethyl-2-chloropyrimidine in place of 2-chloropyrimidine in step (e) and n-nonanal in place of 4-t-butylbenzaldehyde in step (a), the following compounds were prepared:

Example 3

Cis N-(tetrahydropyrimidin-2-yl)-2-methyl-3-(4-t-butylphenyl)pyrrolidine: Hydrochloride

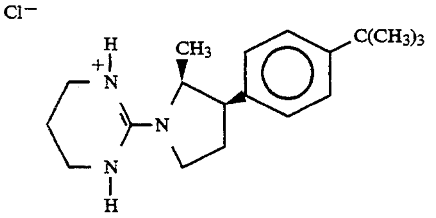

was obtained in a yield of 0.72 g (90 percent of theoretical).

Example 4

Trans N-(tetrahydropyrimidin-2-yl)-2-methyl,3-(4-t-butylphenyl)pyrrolidine: Hydrochloride

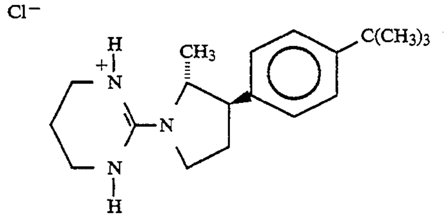

obtained in a yield of 0.24 g (35 percent of theoretical).

Example 5

Cis N-(4,6-dimethyltetrahydropyrimidin-2-yl)-2-methyl-3-(4-t-butylphenyl)-pyrrolidine: Hydrochloride

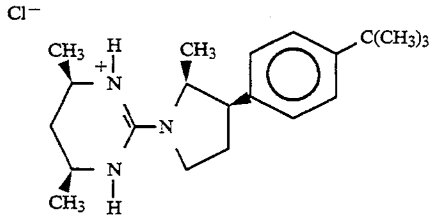

was obtained in a yield of 0.34 g (44 percent of theoretical).

Example 6

Trans N-(4,6-dimethyltetrahydropyrimidin-2-yl)-2-methyl-3-(4-t-butylphenyl)-pyrrolidine: hydrochloride

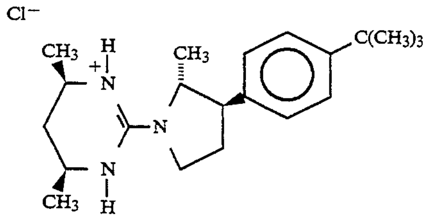

was obtained in a yield of 0.4 g (3percent of theoretical).

Example 7

Cis N-(tetrahydropyrimidin-2-yl)-2-methyl-3-n-octyl pyrrolidine: Hydrochloride

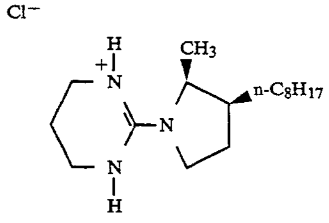

was obtained in a yield of 0.2 g (55 percent of theoretical).

In all cases, NMR and IR spectra of the product were consistent with the expected structure. Additionally, the products of Examples 1–7 were either obtained in the form of an oil or a gum.

The compounds of Formula I and II can be used as fungicides, in particular for agricultural use, against a wide range of pathogens, for example, Ascomycetes, Eumycetes and *Fungi Imperfecti*, in a protectant (control and prevent infestation) or eradicant (kill) fashion. The compounds exhibit low phytotoxicity to crops, in particular cereal and broadleaf crops and in accordance with the invention may be applied to the roots, seeds, or foliage of barley and other plants, for the control of various fungi, without damaging their commercial value. In particular the compounds of the present invention effectively control a variety of undesirable fungi which infest useful plant crops. The compounds are particularly effective against Deutromycotina such as *Septoria nodorum* (glume blotch of cereals), *Pyricularia oryzae* (rice-blast), *Botrytis cinerea* (gray mold of grapes) and *Fusarium oxysporum* (various wilt diseases); Ascomycotina such as *Pyrenophora teres* (net-blotch) and *Erysiphe graminis* (powdery mildew); and Basidiomycotina such as *Puccinia recondita* (leaf rust).

The compounds in accordance with the present invention can be applied to the area where infestation can occur such as seeds, roots or foliage of cereals or other plants and will kill or control the growth of various fungi without damaging the commercial value of said plants.

Where the acid addition salt is employed, the improved water solubility (especially of the chloride) also allows the preparation of solutions (in water or an organic solvent) in which, at use rate, the addition salt is completely soluble in the spray dilution.

At least utilizing the preferred embodiments of the invention a single application of the compositions can provide a residual control of powdery mildew diseases over an extended period. Also, the compounds can be effective in eliminating established barley powdery mildew infestation. Furthermore, many compounds have been found to be translocated in plants and, thus, can provide a systemic protection against powdery mildew.

The compounds of the invention may also find application on non-agricultural fungicides, for example, in medicine as antimycotics against organisms such as *Candida albicans*, Candida spp, Trichophyton spp, Aspergillus spp, Microsporum spp and Sporothrix spp, and also as agents against parasites such as Leishmania.

The method includes within its scope a method for the control or prevention of fungal attack, which method comprises applying to the locus of the fungus, or to a locus in which the infestation is to be prevented, (for example applying to cereal grain plants), a fungicidally effective amount of one or more of the compounds.

The invention also embraces the employment of a liquid, powder, dust or granular composition containing one or more of the active compounds and one or more inert, non-phytotoxic materials, known in the art as agricultural adjuvants and/or carriers in solid or liquid form. Thus, for example, the active compound(s) can be admixed with one or more additives including water or other liquid carriers such as organic solvents, and petroleum distillates, surface active dispersing agents, and finely divided inert solids. In such compositions, the active ingredients are present in a concentration from about 2 percent to about 95 percent by weight, preferably 10 percent to about 95 percent by weight and most advantageously 10 percent to about 75 percent by weight.

The compound can be employed in the form of a solution, a diluted flowable composition or a wettable powder composition containing 2 to 10,000 ppm of active ingredient. Preferably 10 to 600 ppm are employed. When the carrier contains a surface active agent, from about 0.1 to about 20 percent by weight of the active ingredient is advantageously employed. Depending upon the concentration in the composition, such augmented compositions are adapted to be employed for the control of the undesirable fungi or employed as concentrates and subsequently diluted with additional inert carrier, e.g., watery to produce the ultimate treating compositions. In general, good results can be obtained with liquid compositions containing from about 0.0001 to about 2.0 percent by weight of the toxicant in the final diluted form. With dusts, good results can usually be obtained with compositions containing from about 0.1 to about 2.0 percent or more by weight of toxicant.

Where the compositions are to be applied to foliage of plants, it is preferred that the toxicant be present in an amount not to exceed about 0.8 percent in liquid compositions and about 1.0 percent in dusts. In terms of hectarage application, good controls of powdery mildews can be obtained when the active ingredients are applied to growing plants at a dosage of from about 0.004 to about 4 kg/hectare. When employed as fungicides for the treatment of seeds or non-living substrates, from about 0.1 to about 100 grams of active ingredient per kilogram of substrate is an effective dose.

In the preparation of dust, or wettable powder compositions, the toxicant products can be compounded with any of the finely divided solids, such as prophyllite, talc, chalk, gypsum, fuller's earthy bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. Dust compositions are advantageously employed when treating seeds.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsions i.e., a mixture of inert water-immiscible solvent and optional water miscible organic co-solvent, emulsifying agent, and water.

Emulsifiers which can be advantageously employed herein can be readily determined by those skilled in the art and include various nonionic. anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxides, propylene oxide or mixtures of ethylene and propylene oxides such as the ethoxylated alkyl phenols and carboxylic esters solubilized with the polyol or polyoxyalkylene. Cationic emulsifiers include quaternary ammonium compounds and fatty amines. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene; propyl benzene fractions; or mixed naphthalene fractions; mineral oils substituted aromatic organic liquids such as dioctyl phthalate; kerosene, butene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred.

The surface active dispersing agents are usually employed in liquid compositions and in the amount of from 0.1 to 20 percent by weight of the combined weight of the dispersing agent and active compound. The active compositions can also contain other compatible additaments, for example, plant growth regulators and other biologically active compounds used in agriculture.

In particular, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

In such embodiments, the compounds of the present invention or compositions containing the same, can be advantageously employed in combination with one or more additional pesticidal compounds. Such additional pesticidal compounds may be insecticides, nematocides, miticides, arthropodicides, or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additive. The compounds in combination can generally be present in a ratio of from 1:100 to 100:1.

The exact amount of the active material to be applied is dependent not only on the specific active material being applied, but also on the particular action desired, the fungal species to be controlled and the stage of growth thereof as well as the part of the plant to be contacted with the toxic active ingredient. Thus, all of the active ingredients of the present invention and compositions containing the same may not be equally effective at similar concentrations or against the same fungal species.

The compounds in accordance with the invention may be applied in the form of any of the generally used formulation types, for example, as solutions, dusts, wettable powders, flowable concentrates, or emulsifiable concentrates.

Fungicidal Activity Test Procedures

The compounds of Examples 1 to 7 were tested in accordance with the following in vitro and in vivo test methods.

In Vitro Screen Method

Test compounds are dissolved in acetone and made up with distilled water to give a solution with a final concentration of compound of 400 ppm and 10 percent acetone. 2 mL aliquots of the latter solutions are pipetted into sterile petri dishes, and 18 mL of agar is then added to each dish using an automatic agar plate pourer to give a final concentration of compound of 40 ppm.

Once the agar is set, discs of pathogens are cut from stock agar plates using a cork borer, and placed (pathogen face down) onto the test agar surface. Pathogens used in the primary screen include:

1. *Alternaria brassicola*
2. *Fusarium oxysporum phaseolicola*
3. *Pyrenophora teres*
4. *Botrytis cinerea*
5. *Pyricularia oryzae*
6. *Pseudocercosporella herpotrichoides.*

Three pathogens are placed on each plate. Two replicates of each plate are set up and kept in a incubator at 20° C.

The pathogens on plate 1 are assessed after 5 days and those on plate 2 after 8 days. The diameters of the fungal colonies are measured after the incubation period and compared to the control measurements. Allowing for the diameter of the original disc, percentage inhibition values are then calculated.

In Vivo Screen Method

Compounds are dissolved in acetone or water (as required) and made up with distilled water to give a final concentration of compound of 400 ppm (and 10 percent acetone where acetone is used).

For each compound 3 replicate plants per pathogen at the 1 leaf stage are sprayed to run off. The plants are allowed to dry at room temperature for 24 hours prior to inoculation.

Untreated control plants and plants sprayed with 10 percent acetone-water or water alone (as required) are included for each pathogen.

Method for *Erysiphe graminis Hordei*

Barley cv. Golden Promise is used as the host plant. Seeds are sown 8 per 3" pot and allowed to germinate and the plants are treated when they are approximately 2 weeks old. Spores are blown onto the test plants from the stock plants, which are then incubated at 20° C., relative humidity 70 percent for 7 days. After a week symptoms are recorded. The percent infection is scored from 3 replicate plants and expressed as a percent of the infection on the acetone-water control plants. The percent control is then recorded.

Method for *Puccinia recondita*

Wheat cv. Tonic is used as the host plant. Seeds are sown 1 cm deep in 4 rows per plastic tray. The tray is 60 cm×30 cm. Seedlings grown to the 1-2 leaf stage are then inoculated. 0.05 g of uredospores are put into 100 mL of distilled water with a melting agent. This solution is sprayed onto the seedlings leaving a fine coverage on the leaves. The plants are then incubated with 100 percent relative humidity at 15°20° C. for 4 days.

Percent infection is scored from 3 replicate plants and expressed as a percent of the infection on acetone-water control plants. Percent control is then recorded.

The results are shown in Tables 1 and 2 respectively.

TABLE 1

Percent Efficacy of Compounds of Examples 1 to 7 in In vitro Biological Evaluation

| Example Number | *Alternaria brassicola* | *Fusarium oxysporum* | *Pyrenophora teres* | *Pseudocercosporella herpotrichoides* | *Botrytis cinerea* | *Pyricularia oryzae* |
|---|---|---|---|---|---|---|
| 1 | 81 | 74 | 100 | NT | 33 | 90 |
| 2 | 61 | 90 | 95 | NT | 49 | 65 |
| 3 | NT | 68 | 100 | 50 | NT | 68 |
| 4 | NT | 86 | 78 | 33 | NT | 47 |
| 5 | NT | 79 | 84 | 67 | NT | 63 |
| 6 | NT | 80 | 75 | 58 | NT | 63 |
| 7 | NT | 84 | 92 | 82 | NT | 85 |

NT - Not Tested

TABLE 2

Percent Efficacy of Compounds of Examples 1 to 7 in In vitro Biological Evaluation

| Example Number | *Erysiphe graminis* | *Puccinia recondita* | Percent Phytotoxicity to Host Plants |
|---|---|---|---|
| 1 | 100 | 0 | 0 |
| 2 | 83 | 0 | 0 |
| 3 | 14 | 100 | 0 |
| 4 | 87 | 66 | 0 |
| 5 | 52 | 100 | 0 |
| 6 | 100 | 0 | 0 |
| 7 | 79 | 0 | 0 |

NT - Not Tested

What is claimed is:

1. A compound corresponding to the formula

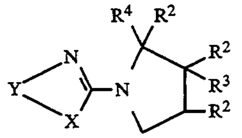

I or an agriculturally acceptable salt of the compounds of Formula I corresponding to the general formula,

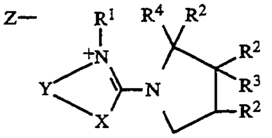

II $R^1$ is hydrogen or $C_1$–$C_3$ alkyl;

$R^2$, each independently, is hydrogen or $C_1$–$C_4$ alkyl;

$R^3$ is a $C_4$–$C_{20}$ alkyl group, a $C_4$–$C_{20}$ alkenyl group, a phenyl group, a phenyl-$C_1$–$C_3$ alkylene group or a phenyl-$C_2$–$C_3$ alkenylene group wherein the phenyl ring can be substituted with from 1 to 5 halogen atoms, $C_1$–$C_6$ alkyl, $C_1$–$C_6$ alkoxy groups, trihalomethyl groups, phenyl groups or phenoxy groups;

$R^4$ is hydrogen or $C_1$–$C_4$ alkyl;

X is a group of the formula —$C(R^7R^7)$—, wherein each $R^7$ independently is hydrogen, $C_1$–$C_4$ alkyl, $C_1$–$C_4$ hydroxyalkyl, $C_2$–$C_4$ alkoxyalkyl or a group of the formula $$—(CH_2)_q—O—C(O)—R^8$$

wherein q is the integer 1, 2 or 3, and $R^8$ is methyl or ethyl or X is a group of the formula —$N(R^9)$—, wherein $R^9$ is H, or $C_1$–$C_3$ alkyl;

Y is a group of the formula —$(CR^7R^7)_n$—, wherein each $R^7$ independently is as defined above, n is the integer 2, 3, or 4; and Z is an anion from the group consisting of the bromide, chloride, iodide, acetate, stearate, benzoate, and dodecylbenzenesulphonate.

2. The compound as claimed in claim 1 which is cis N-(tetrahydropyrimidin-2-yl)-2-methyl-3-(4-t-butylphenyl)pyrrolidine: acetic acid-salt.

3. The compound as claimed in claim 1 which is trans N-(tetrahydropyrimidin-2-yl)-2-methyl-3-(4-t-butylphenyl)pyrrolidine: acetic acid salt.

4. The compound as claimed in claim 1 which is cis N-(tetrahydropyrimidin-2-yl)-2-methyl-3-(4-t-butylphenyl)pyrrolidine: hydrochloride.

5. The compound as claimed in claim 1 which is trans N-(tetrahydropyrimidin-2-yl)-2-methyl-3-(4-t-butylphenyl)pyrrolidine: hydrochloride.

6. The compound as claimed in claim 1 which is cis N-(4,6-dimethyltetrahydropyrimidin-2-yl)-2-methyl-3-(4-t-butylphenyl)pyrrolidine: hydrochloride.

7. The compound as claimed in claim 1 which is trans N-(4,6-dimethyltetrahydropyrimidin-2-yl)-2-methyl-3-(4-t-butylphenyl)pyrrolidine: hydrochloride.

8. A fungicidal composition comprising an inert carrier or diluent in admixture with a compound corresponding to the formula

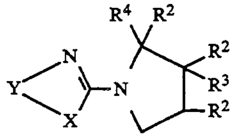

I or an agriculturally acceptable salt of the compounds of Formula I corresponding to the general formula,

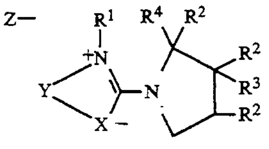

II wherein $R^1$ is hydrogen or $C_1$–$C_3$ alkyl, $R^2$, each independently, is hydrogen or $C_1$–$C_4$ alkyl;

$R^3$ is a $C_4$–$C_{20}$ alkyl group, a $C_4$–$C_{20}$ alkenyl group, a phenyl group, a phenyl–$C_1$–$C_3$ alkylene group or a phenyl–$C_2$–$C_3$ alkenylene group wherein the phenyl ring can be substituted with from 1 to 5 halogen atoms, $C_1$–$C_6$ alkyl, $C_1$–$C_6$ alkoxy groups, trihalomethyl groups, phenyl groups or phenoxy groups;

$R^4$ is hydrogen or $C_1$–$C_4$ alkyl;

X is a group of the formula $—C(R^7R^7)—$, wherein each $R^7$ independently is hydrogen, $C_1$–$C_4$ alkyl, $C_1$–$C_4$ hydroxyalkyl, $C_2$–$C_4$ alkoxyalkyl or a group of the formula $$—(CH_2)_q—O—C(O)—R^8,$$

wherein q is the integer 1, 2 or 3, and $R^8$ is methyl or ethyl or X is a group of the formula $—N(R^9)—$, wherein $R^9$ is H, or $C_1$–$C_3$ alkyl;

Y is a group of the formula $—(CR^7R^7)_n—$, wherein each $R^7$ independently is as defined above, n is the integer 2, 3, or 4; and Z is an anion from the group consisting of the bromide, chloride, iodide, acetate, stearate, benzoate, and dodecylbenzenesulphonate.

9. A composition as claimed in claim 8 wherein the active compound is cis N-(tetrahydropyrimidin-2-yl)-2-methyl-3-(4-t-butylphenyl)pyrrolidine: acetic acid salt.

10. A composition as claimed in claim 8 wherein the active compound is trans N-(tetra-hydropyrimidin-2-yl)-2-methyl-3-(4-t-butylphenyl)pyrrolidine: acetic acid salt.

11. A composition as claimed in claim 8 wherein the active compound is cis N-(tetra-hydropyrimidin-2-yl)-2-methyl-3-(4-t-butylphenyl)pyrrolidine: hydrochloride.

12. A composition as claimed in claim 8 wherein the active compound is trans N-(tetra-hydropyrimidin-2-yl)-2-methyl,3-(4-t-butylphenyl)pyrrolidine: hydrochloride.

13. A composition as claimed in claim 8 wherein the active compound is cis N-(4,6-dimethyltetrahydropyrimidin-2-yl)-2-methyl-3-(4-t-butylphenyl)pyrrolid hydrochloride.

14. A composition as claimed in claim 8 wherein the active compound is trans N-(4,6-dimethyltetrahydropyrimidin-2-yl)-2-methyl-3-(4-t-butylphenyl)pyrrolidine: hydrochloride.

15. A composition as claimed in claim 8 which is in the form of a solution, a dust, an emulsifiable concentrate, or a wettable powder.

16. A method for the kill and control of fungal organisms which infest plants which comprises applying to the fungi or to the area where infestation is to be prevented, a fungicidally effective amount of a composition comprising an inert carrier or diluent in admixture with a compound corresponding to the formula

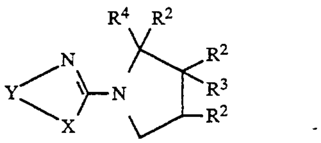

I or an agriculturally acceptable salt of the compounds of Formula I corresponding to the general formula,

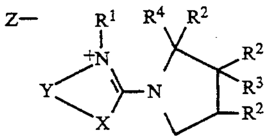

II wherein $R^1$ is hydrogen or $C_1$–$C_3$ alkyl;

$R^2$, each independently, is hydrogen or $C_1$–$C_4$ alkyl;

$R^3$ is a $C_4$–$C_{20}$ alkyl group, a $C_4$–$C_{20}$ alkenyl group, a phenyl group, a phenyl–$C_1$–$C_3$ alkylene group or a phenyl–$C_2$–$C_3$ alkenylene group wherein the phenyl ring can be substituted with from 1 to 5 halogen atoms, $C_1$–$C_6$ alkyl, $C_1$–$C_6$ alkoxy groups, trihalomethyl groups, phenyl groups or phenoxy groups;

$R^4$ is hydrogen or $C_1$–$C_4$ alkyl;

X is a group of the formula $—C(R^7R^7)—$, wherein each $R^7$ independently is hydrogen, $C_1$–$C_4$ alkyl $C_1$–$C_4$ hydroxyalkyl, $C_2$–$C_4$ alkoxyalkyl or a group of the formula $$—(CH_2)_q—O—C(O)—R^8,$$

wherein q is the integer 1, 2 or 3, and $R^8$ is methyl or ethyl or X is a group of the formula $—N(R^9)—$, wherein $R^9$ is H, or $C_1$–$C_3$ alkyl;

Y is a group of the formula $—(CR^7R^7)_n—$, wherein each $R^7$ independently is as defined above, n is the integer 2, 3, or 4; and Z is an anion from the group consisting of the bromide, chloride, iodide, acetate, stearate, benzoate, and dodecylbenzenesulphonate.

17. A method as claimed in claim 16 wherein the active compound is cis N-(tetrahydropyrimidin-2-yl)-2-methyl-3-(4-t-butylphenyl)pyrrolidine: acetic acid salt.

18. A method as claimed in claim 16 wherein the active compound is trans N-(tetrahydropyrimidin-2-yl)-2-methyl-3-(4-t-butylphenyl)pyrrolidine: acetic acid salt.

19. A method as claimed in claim 16 wherein the active compound is cis N-(tetrahydropyrimidin-2-yl)-2-methyl-3-(4-t-butylphenyl)pyrrolidine: hydrochloride.

20. A method as claimed in claim 16 wherein the active compound is trans N-(tetrahydropyrimidin-2-yl)-2-methyl,3-(4-t-butylphenyl)pyrrolidine: hydrochloride.

21. A method as claimed in claim 16 wherein the active compound is cis N-(4,6-dimethyltetrahydropyrimidin-2-yl)-2-methyl-3-(4-t-butylphenyl)pyrrolidine: hydrochloride.

22. A method as claimed in claim 16 wherein the active compound is trans N-(4,6-dimethyltetrahydropyrimidin-2-yl)-2-methyl-3-(4-t-butylphenyl)pyrrolidine: hydrochloride.

* * * * *